(12) United States Patent
Ritter

(10) Patent No.: US 7,494,278 B2
(45) Date of Patent: Feb. 24, 2009

(54) METHOD FOR CORRECTING NON-REPRODUCIBLE GEOMETRIC ERRORS OCCURRING DURING OPERATION OF A C-ARM DEVICE

(75) Inventor: Dieter Ritter, Fürth (DE)

(73) Assignee: Siemens Aktiengesellschaft, Munich (DE)

( * ) Notice: Subject to any disclaimer, the term of this patent is extended or adjusted under 35 U.S.C. 154(b) by 28 days.

(21) Appl. No.: 11/814,486

(22) PCT Filed: Jan. 23, 2006

(86) PCT No.: PCT/EP2006/050368

§ 371 (c)(1),
(2), (4) Date: Jul. 23, 2007

(87) PCT Pub. No.: WO2006/082146

PCT Pub. Date: Aug. 10, 2006

(65) Prior Publication Data

US 2008/0192884 A1   Aug. 14, 2008

(30) Foreign Application Priority Data

Feb. 3, 2005   (DE) .................. 10 2005 005 087

(51) Int. Cl.
*G01D 18/00*   (2006.01)

(52) U.S. Cl. ..................................... 378/207; 378/197
(58) Field of Classification Search .................. 378/4, 378/19, 196, 197, 198, 207
See application file for complete search history.

(56) References Cited

U.S. PATENT DOCUMENTS

| | | | |
|---|---|---|---|
| 6,379,041 B1 * | 4/2002 | Schuetz et al. | 378/205 |
| 7,147,373 B2 * | 12/2006 | Cho et al. | 378/207 |
| 2007/0238986 A1 * | 10/2007 | Graumann | 600/424 |

* cited by examiner

*Primary Examiner*—Chih-Cheng G Kao
(74) *Attorney, Agent, or Firm*—Schiff Hardin LLP

(57) ABSTRACT

In a method for correcting non-reproducible geometric errors occurring during the operation of an x-ray C-arm device, having a C-arm carrying an x-ray source, during orbital displacement of the C-arm during a scan for 3D reconstruction of a subject volume, a 2D dataset, which is not impaired by non-reproducible geometric errors during the scan, is determined. This 2D dataset is compared to known projection matrices of the x-ray C-arm device, which compensate reproducible geometric errors of the C-arm device. The result of the comparison is used to modify the projection matrices of the scan to compensate non-reproducible geometric errors that occur during the scan.

6 Claims, 3 Drawing Sheets

METHOD FOR CORRECTING NON-REPRODUCIBLE GEOMETRIC ERRORS OCCURRING DURING OPERATION OF A C-ARM DEVICE

BACKGROUND OF THE INVENTION

1. Field of the Invention

The present invention concerns a method for correction of non-reproducible geometry errors of an x-ray C-arm, which occur due to orbital movement of the C-arm during a scan implemented for 3D reconstruction of a patient volume.

2. Description of the Prior Art

An x-ray C-arm apparatus of this type has a base frame on which the C-arm is supported such that it can move orbitally around an isocenter. One end of the C-arm carries an x-ray source and the other end an x-ray receiver, for example a planar detector. Such apparatuses (used in a mobile or stationary manner) are used for, among other things, the 3D reconstruction of a patient volume. 3D exposures are acquired from a number of different angle positions and the patient volume of interest is reconstructed with known calculation methods. The image quality of 3D reconstructions is decisive for its usability, for example for diagnostic purposes. An important parameter for error-free imaging of the 3D world in a 2D image plane is the optimally error-free reproducibility of the position and orientation of the x-ray receiver relative to the isocenter of the C-arm. Due to its own mass and the masses of x-ray source and x-ray receiver, the C-arm twists more or less severely depending on the orbital position. These distortions (that can lie in the centimeter range) are typically compensated in that the movement track of the C-arm is calibrated in an offline method. For this purpose the projection matrices of the C-arm or, respectively, of the x-ray system borne by it are determined using a calibration phantom. Mechanical distortions of the C-arm that occur in at least approximately the same manner given every orbital movement of the C-arm can thereby be compensated. Depending on the type of bearing and drive of the C-arm, a non-reproducible wobbling of the C-arm (ascribed, for example, to tolerance-dependent play) cannot be avoided. A geometry error caused by wobbling leads to a limitation of the spatial resolution to values of approximately 7 to 10 lp/cm for a scan implemented for 3D reconstruction of a patient volume.

SUMMARY OF THE INVENTION

An object of the invention is to provide a method for correction of non-reproducible geometry errors in such C-arm systems.

This object is achieved according to the invention by a method in which a 2D data set impaired by a non-reproducible geometry error during the scan is determined; this data set is compared with the known projection matrices of the x-ray C-arm apparatus which compensate for reproducible geometry errors of the C-arm apparatus; and the result of this comparison is utilized to alter the projection matrices of the scan so that a non-reproducible geometry error occurring during the scan is compensated. The 2D data set determined in one of the methods described further below can be compared with the known projection matrices in a simple manner via known methods and a correction of the 2D data set can be effected. An increase of the resolution of the 2D data sets and correspondingly a 3D reconstruction generated from these can be achieved in this manner.

In a preferred method variant a sinogram reflecting a trajectory T1 of a subject is generated during a scan of the high-contrast subject arranged within a patient volume, which scan is implemented for 3D reconstruction of the patient volume. A trajectory T2 of a virtual subject point is generated from known projection matrices of the C-arm apparatus that already compensate for reproducible geometry errors and the difference function between the trajectory T1 and the trajectory T2 is determined. The difference function now corresponds precisely to the non-reproducible portion of the C-arm movement, such that the projection matrices of the scan effected on the patient can be optimized such that a non-reproducible geometry error of the C-arm that does not occur during a scan is compensated. An advantage of such a method is that a geometry correction can thus be improved without technical expenditure on the part of the apparatus in a simple manner with the aid of known and frequently used algorithms from the field of 3D reconstruction. Moreover, the inventive method makes it possible to use C-arm apparatuses with lower requirements for their mechanical stability or for the movement precision of the C-arm.

In principle it is possible to implement the proposed correction of geometry errors with the aid of 2D sinograms. However, in a preferred method a 3D sinogram is generated which supplies information about the spatial coordinates of a non-reproducible path deviation of the C-arm or of the x-ray system supported thereby. The generation of the trajectory T2 is advantageously based on projection matrices which were acquired with the aid of a calibration phantom on the C-arm apparatus.

In a further preferred method variant a first 2D data set acquired for a first orbital position of the x-ray source is correlated with a second 2D data set acquired given a subsequent second orbital position during a scan. If a deviation between the two 2D data sets exists that is not dependent on the different orbital positions, the second 2D data set is compared with the known projection matrices of the second orbital position and the result of this comparison is used to alter the projection matrices of the second 3D data set for compensation of a non-reproducible geometry error. In this method variant, no sinogram is generated from individual 2D exposures made at different orbital positions of the x-ray radiator apparatus; rather, successive 2D data sets in the movement direction of the C-arm are compared with one another and a comparison of the respective incorrect 2D data sets with the known projection matrices and a corresponding correction are effected given a significant deviation. Here as well known methods and algorithms can be used.

It is conceivable to apply the proposed method variants to a correction of further degrees of freedom of movement of the C-arm. However, non-reproducible geometry errors are advantageously only corrected in a plane proceeding at a right angle to the projection axis of the C-arm apparatus. Path deviations in this plane reduce the spatial resolution significantly more strongly than deviations in the remaining degrees of freedom of movement of the C-arm. A correction in the cited plane is possible with relatively slight computation effort. In contrast to this, a correction of further degrees of freedom of movement would entail only a comparably slight improvement of the spatial resolution of a 3D reconstruction given a high computation effort.

DESCRIPTION OF THE PREFERRED EMBODIMENTS

Figure 1:
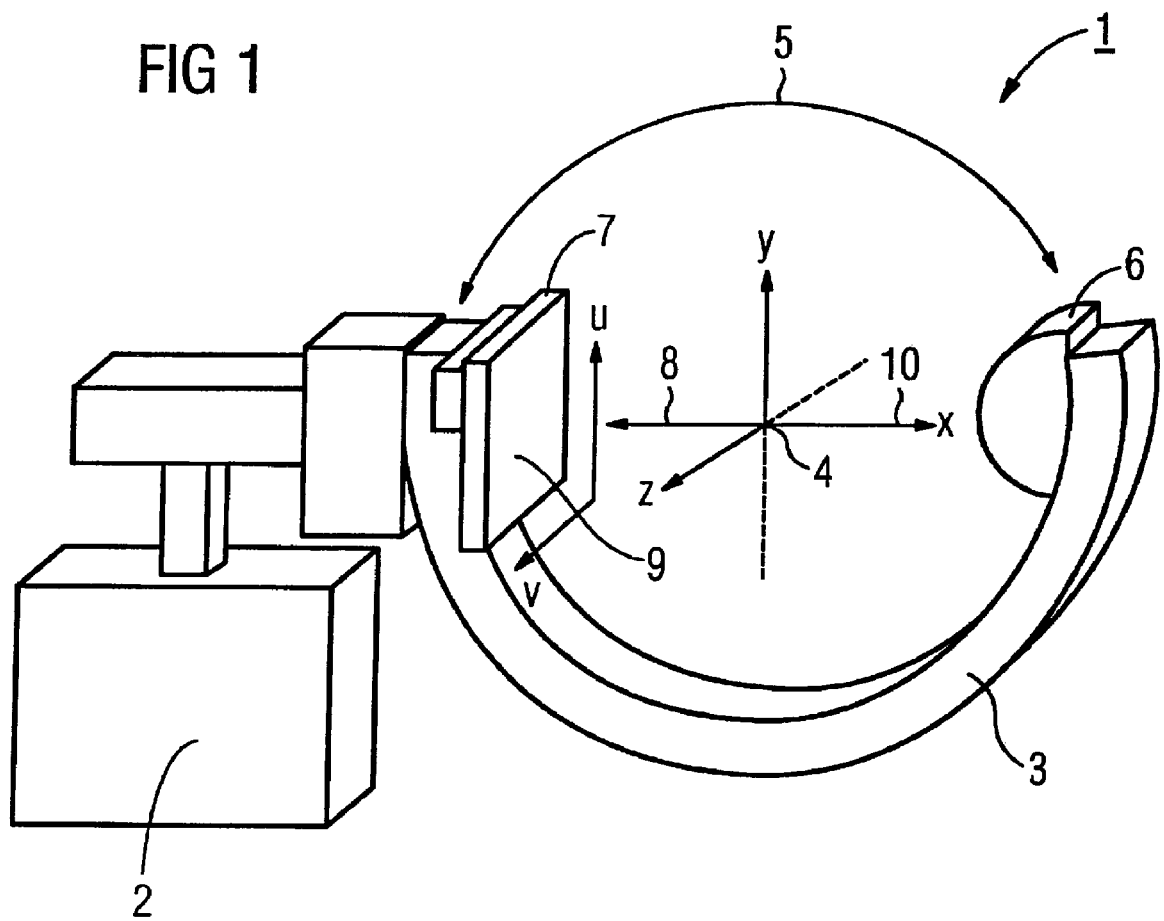
FIG. 1 is a schematic representation of an x-ray C-arm apparatus.

The x-ray C-arm apparatus (called C-arm apparatus 1 in the following for short) shown in FIG. 1 is mobile or stationary and comprises a base frame 2 on which a C-arm 3 is supported such that it can move in an orbital direction 5 around an isocenter 4. An x-ray source 6 is arranged at one end of the C-arm 3 and a planar detector 7 is arranged as an x-ray receiver at the diametrically-opposite end. The radiation or, respectively, projection axis 8 of the x-ray source 7 intersects the isocenter 4 given an ideal geometry. The acquisition surface 9 (formed from a number of individual detectors) of the planar detector 7 extends at a right angle to the projection axis 8 or, respectively, at a right angle to the spatial axis designated with X in FIG. 1 and is established by the coordinate axes u and v of the C-arm 1.

Figure 2:
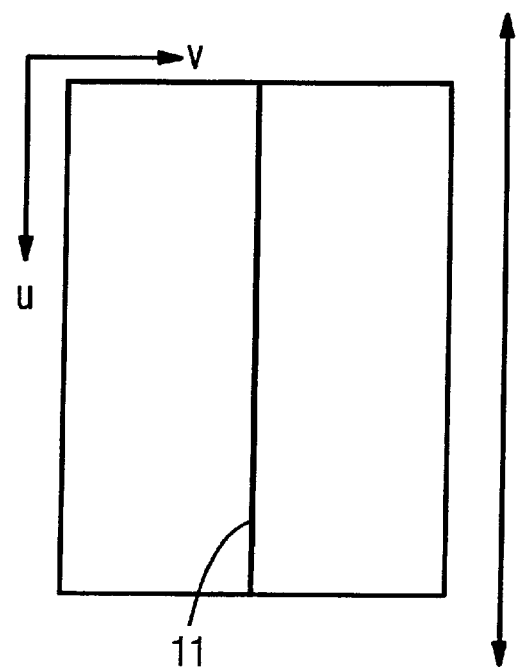
FIG. 2, 3 are schematic representations to explain the generation of a sinogram.
Figure 3:
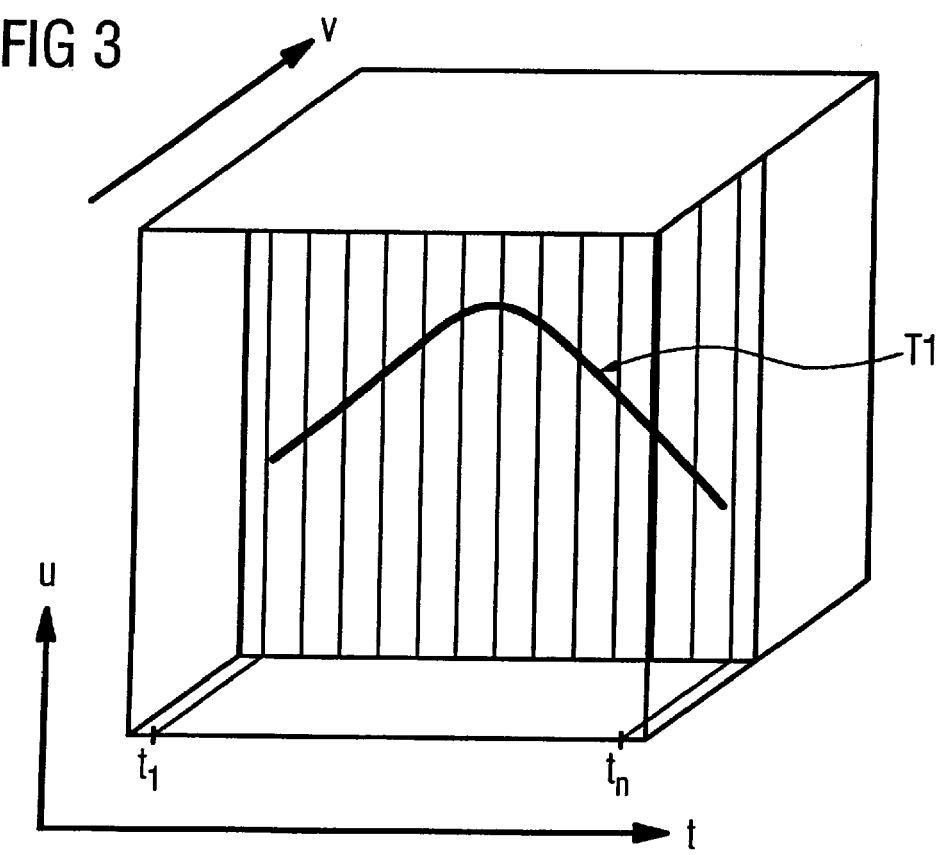
Figure 4:
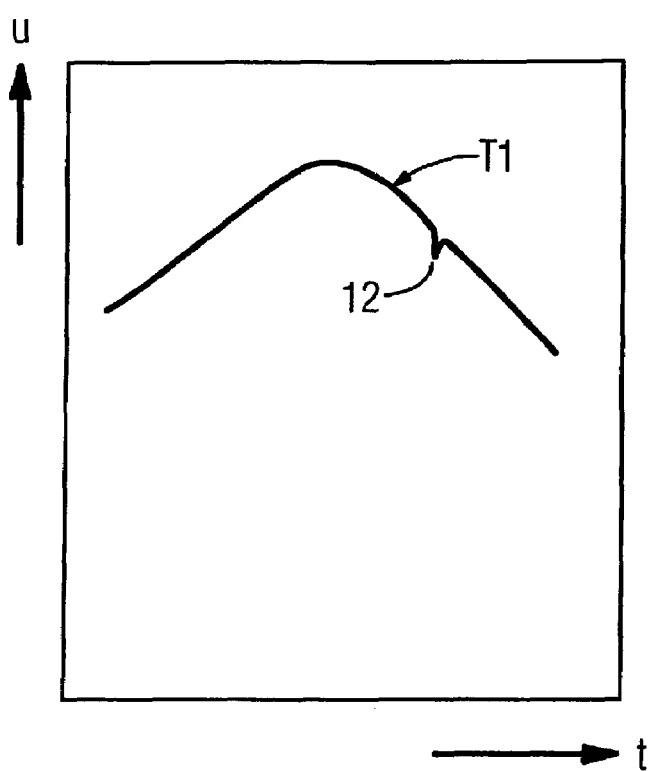
FIG. 4 shows a sinogram acquired during a patient scan.
Figure 5:
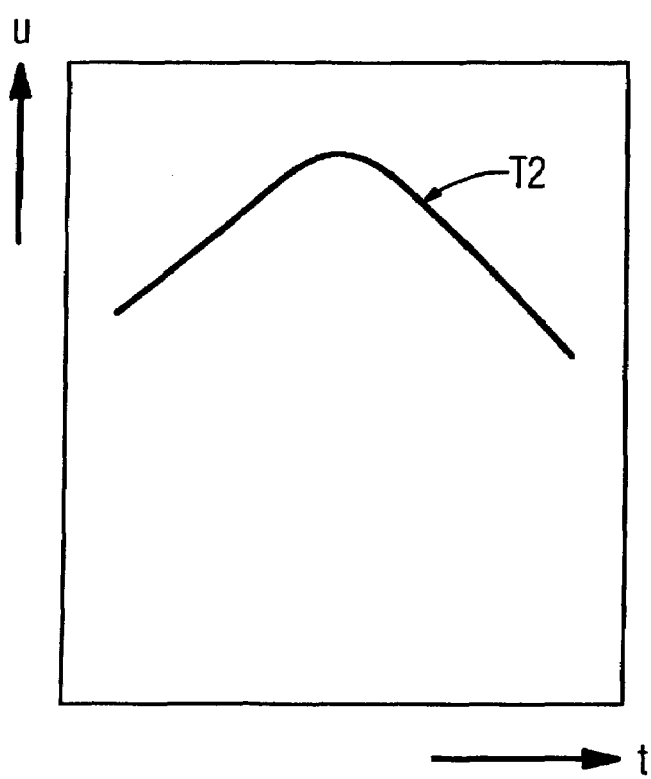
FIG. 5 shows an averaged sinogram of a C-arm apparatus acquired using a calibration phantom.

During the 3D reconstruction of a patient volume, a patient is located on a table (not shown) such that the isocenter 4 is located within the body region of interest. Starting from the start position shown in FIG. 1, the C-arm 3 is moved clockwise in the orbital direction 5 until its end position and thereby generates a number of 2D data sets of the patient volume. For such a scan, a 3D sinogram of an easily-identifiable subject of the patient volume is now acquired. Suitable subjects for this are, for instance, bones, air enclosed in colon, stomach or lungs, vessels enriched with contrast agents, orthopedic endoprostheses and markers. Either a punctiform subject or the edge of a high-contrast subject (for instance the border region of a bone) is now tracked during a scan to generate the 3D sinogram. During a scan the projection of a subject point (provided with the reference character 10 in FIG. 1) passes through a detector line 11 (FIG. 2) extending in the direction of the u-axis given an orbital movement of the C-arm 3 on the acquisition surface 9 of the planar detector 7. If such a detector line 11 is plotted over the time t, given a maximum travel angle of the C-arm 3 a curve of approximately 190° results that approximately corresponds to half a sine curve. The individual time segments $t_1$ through $t_n$ thereby correspond to different orbital positions of the x-ray source 6 or of the planar detector 7 or to different alignments of the projection axis 8 relative to the subject point 10. If only one detector line corresponding to FIG. 3 is plotted, a 2D sinogram arises which can be extracted from the relative movement of the subject point 10 or its projection onto the acquisition surface 9 in the form of a trajectory T1. Assuming that the subject point 10 lay in the orbital plane of the C-arm 3 spanned by the x- and y-coordinates, a geometry error acting only in this plane would be recognizable as a more or less strongly pronounced deviation 12 (FIG. 4) from the curve course of the trajectory T1. In contrast to this, a wobbling acting at a right angle to the orbital plane or in the direction of the v-axis would be less well recognizable, for instance as an interruption of the curve course of the trajectory T1, because the deviation 12 would effectively extend out from the paper plane or into this. However, if a 3D sinogram is acquired which implements a plurality of further detector lines flanking the detector line 11 in the direction of the v-axis (not shown in FIG. 3), the cited path deviations of the C-arm 3 (acting in the present case from the orbital plane in the z-direction or in the direction of the v-axis) can also be recognized and quantitatively detected.

In comparison to CT scanners, a somewhat less sturdy mechanism for the orbital revolution of the x-ray source 6 an the x-ray receiver is used in x-ray C-arm apparatuses. For example, the open shape of the C-arm entails that this widens in the situation shown in FIG. 1, whereby the projection axis 8 experiences a slight inclination relative to the x-axis. Therefore x-ray C-arm apparatuses used for 3D reconstructions must be calibrated in an offline method. The projection matrices are thereby determined once using a calibration phantom. A number of orbital movements are effected in order to eliminate non-reproducible geometry errors.

For correction of non-reproducible geometry errors occurring during a patient scan, these projection matrices are now resorted to and a trajectory T2 of a virtual subject point is generated. The subject point is thereby located in the region of the isocenter 4 or in a space that corresponds to the patient volume to be reconstructed. The trajectory T2 corresponds to the trajectory T1 except for phase, amplitude, offset and deviation 12. A fit of both trajectories T1 and T2 in these three parameters directly yields the difference function between T1 and T2. The difference function now precisely corresponds to the non-reproducible portion of the C-arm movement and allows the projection matrices determined during an offline calibration to be corrected so that a non-reproducible path deviation of the C-arm is eliminated. Another possibility to eliminate non-reproducible path deviations with the aid of the cited difference function is to interpret the deviation of the two trajectories T1 and T2 in the direction of the u-axis and the v-axis as a corresponding translation of the planar detector 7.

A further possibility to detect the occurrence of a non-reproducible geometry error provides that during a patient scan successive 2D exposures or 2D data sets, thus 2D exposures or 2D data sets made in successive orbital positions of the x-ray system (in particular of a planar detector 7) in the movement direction of the C-arm, are correlated with one another. Due to the number of the 2D data sets generated during a scan, two successive 2D data sets differ only slightly with regard to the acquisition angle or the x-ray radiation direction, such that an image point alters its position in the direction of the u-axis and/or v-axis only by a slight measure (and which measure is known due to the known C-arm geometry) relative a preceding 2D data set. However, if a geometry error (for example as a series of wobbles) occurs given the movement of the C-arm from the one orbital position to the next, the position deviation of an image point resulting from this is significantly larger and thus such an event can easily be recognized. As in the first described method variant, here as well the known projection matrices of the respective C-arm are resorted to for correction or, respectively, compensation of the occurred error and a correction of the incorrect 2D data set is effected, whereby known methods and algorithms are again available for this purpose.

Although modifications and changes may be suggested by those skilled in the art, it is the invention of the inventor to embody within the patent warranted heron all changes and modifications as reasonably and properly come within the scope of his contribution to the art.

I claim as my invention:

1. A method for correcting non-reproducible geometry errors during operation of an x-ray C-arm apparatus having a C-arm on which an x-ray source and an x-ray detector are mounted, said non-reproducible geometry errors occurring during orbital movement of said C-arm during a scan implemented for 3D reconstruction of a subject volume, comprising the steps of:

during said scan, determining a 2D dataset impaired by a non-reproducible geometry error;

comparing said 2D dataset with known projection matrices for said x-ray C-arm apparatus that compensate reproducible geometry errors due to said orbital movement of said C-arm, thereby obtaining a comparison result; and automatically using said comparison result to modify said projection matrices of said scan to compensate said non-reproducible geometry error.

2. A method as claimed in claim 1 comprising:

generating a sinogram representing a trajectory T1 of a high-contrast subject during a scan involving said orbital movement of said C-arm;

generating a trajectory T2 of a virtual subject point from said known projection matrices; and automatically determining a difference function between said trajectory T1 and said trajectory T2, and using said difference function to modify said projection matrices to compensate for said non-reproducible geometry error.

3. A method as claimed in claim 2 comprising generating said sinogram as a 3D sinogram.

4. A method as claimed in claim 2 comprising generating said trajectory T2 based on projection matrices acquired with a calibration phantom using said C-arm apparatus.

5. A method as claimed in claim 1 comprising:

acquiring a first 2D dataset during a scan at a first orbital position of said x-ray source, and acquiring a second 2D dataset, correlated to said first 2D dataset, at a subsequently assumed second orbital position;

determining an existence of a deviation between said first and second 2D datasets that is not caused by said first and second orbital positions being different and, if said deviation exists, comparing said second 2D dataset with said known projection matrices of said second orbital position to obtain a further comparison result; and using said further comparison result to alter the projection matrices of said second 2D dataset to compensate said non-reproducible geometry error.

6. A method as claimed in claim 1 comprising correcting only geometry errors that occur in a plane proceeding at a right angle to a projection axis of said C-arm apparatus.

* * * * *